United States Patent
Chuang

(10) Patent No.: US 6,536,277 B1
(45) Date of Patent: Mar. 25, 2003

(54) LEVEL-TRACING WATER-MONITORING APPARATUS

(75) Inventor: Hsu-Chen Chuang, Shin-Dian (TW)

(73) Assignee: Taiwan Water & Soil Instrumentation, Inc. (TW)

( * ) Notice: Subject to any disclaimer, the term of this patent is extended or adjusted under 35 U.S.C. 154(b) by 0 days.

(21) Appl. No.: 10/015,454

(22) Filed: Dec. 12, 2001

(51) Int. Cl.[7] .............................................. G01F 23/00
(52) U.S. Cl. ........................... 73/319; 73/313; 73/314; 73/305; 73/307; 73/309; 73/318; 340/623; 340/624; 340/625
(58) Field of Search ........................... 73/319, 313, 314, 73/305, 307, 309, 318; 340/623, 624, 625

(56) References Cited

U.S. PATENT DOCUMENTS

| | | | | |
|---|---|---|---|---|
| 711,521 A | * | 10/1902 | Parmelee | 73/311 |
| 2,708,256 A | * | 5/1955 | Colt | 318/6 |
| 3,148,542 A | * | 9/1964 | Clift | 73/313 |
| 3,685,358 A | * | 8/1972 | Hubner et al. | 73/321 |
| 3,713,224 A | * | 1/1973 | Bengoa | 33/715 |
| 4,236,144 A | * | 11/1980 | Sunagawa | 340/870.18 |
| 4,313,114 A | * | 1/1982 | Lee et al. | 340/870.23 |
| 4,571,998 A | * | 2/1986 | Stegner | 73/321 |
| 5,144,836 A | * | 9/1992 | Webb | 73/319 |
| 5,164,605 A | * | 11/1992 | Kidwell | 116/228 |
| 5,483,831 A | * | 1/1996 | Steiner | 73/313 |
| 5,533,392 A | * | 7/1996 | Kira | 73/290 B |
| 5,950,487 A | * | 9/1999 | Maresca et al. | 73/293 |

* cited by examiner

Primary Examiner—Daniel S. Larkin
Assistant Examiner—André K. Jackson

(57) ABSTRACT

A water-monitoring apparatus includes a frame being installed by water. A reel is mounted on the frame. A tension cable is wound on the reel and including a lower end and an upper end. A buoy is connected with the tension cable. A control device is connected with the reel. When the water level changes, the control device rotates the reel so as to adjust a length of the tension cable extending from the reel for allowing the buoy to just float on the water surface. A detecting device is carried via the buoy for detecting at least one environmental characteristic and for producing at least one signal representative of the at least one environmental characteristic. A signal wire is electrically connected with the detecting device. The signal wire includes a helical section for automatically adjusting a distance between its two ends according to the position of the buoy. A monitor device is electrically connected with the signal wire.

19 Claims, 6 Drawing Sheets

LEVEL-TRACING WATER-MONITORING APPARATUS

BACKGROUND OF INVENTION

1. Field of Invention

The present invention relates to monitoring of water quality and, more particularly, to a level-tracing water-monitoring apparatus.

2. Prior Art

While developing, the world is encountering a serious problem of pollution. Water pollution could be the worst among all types of pollution. A lot of pollutants are dumped to reservoirs and open channels from fixed sources such as factories and farms, or from mobile sources such as vehicles. In some cases, such pollutants are directly released into water. In some other cases, such pollutants are disposed of on the ground and then washed into the water by rain. Once introduced into the water, such pollutants inevitably increase costs in treating the water and very often harm human bodies, life stock and aquatic lives.

Before any proper measure can be taken to solve the problem of water pollution, by what pollutants and to what extent the water is polluted must be analyzed. In other words, various quality parameters of the water must be detected.

In early days, prior to analyses, water was manually sampled. Manual sampling has always been expensive and cumbersome. Therefore, manual sampling was conducted on an irregular basis and rarely.

To achieve regular and frequent sampling, it must be done automatically. There have been installed some conventional monitoring stations into which water is automatically pumped through pipes. It is, however, found difficult to have the pipes catch up with the water level changing vigorously from season to season. When the water level becomes too low for the pipes to reach, it is impossible to pump water through the pipes.

To continuously monitor the water, some water-monitoring apparatuses have been devised with sensors are carried by means of a buoy tied to a bank or a well by means of a cable. To have the buoy float on the water when the water level is low, a sufficiently long cable is used. However, the cable allows the buoy to drift for a long distance in any direction when the water level is high. As the buoy drifts, the cable often tangles with miscellaneous objects, e.g., twigs. This could seriously affect the operation of the sensors.

To prevent the cable from tangling with miscellaneous objects, there has been devised a length control device in which the cable is wound on a reel operatively connected with a motor. The motor can be activated to rotate the reel to adjust a length of the cable extending from the reel so that the sensors can always be immerged in water. However, the motor consumes a lot of energy.

In addition, to transmit signals from the sensors to a monitoring station, the cable is connected to the monitoring station through a signal relay including a mandrel electrically connected with the cable. The mandrel rotates together with the reel. The signal relay further includes a brush electrically connected with the monitoring station. The brush does not rotate. The mandrel is in rotational engagement with the brush, thus allowing the mandrel to rotate with respect to the brush while allowing the signals to be transmitted from the mandrel to the brush. However, friction between the mandrel and the brush interferes with the rotation of the reel and wears out the brush after serving for a period of time.

In a co-pending patent application, the inventor teaches a water-monitoring apparatus including a length control device and a non-contact relay. The length control device includes a reel on which a cable is wound. A buoy is connected with the cable. A sensor is used to detect a water quality parameter and to produce a signal representative of the water quality parameter. The sensor is carried by means of the buoy and electrically connected with the cable. The reel can be rotated to adjust a length of the cable extending from the reel so that the sensor can always be immersed in the water. The non-contact relay includes a transmitter and a receiver. The transmitter is electrically connected with the cable and rotated together with the reel. The receiver is installed in a proper position by the water. The transmitter and the receiver are in non-contact communication of signal with each other. Such a water-monitoring apparatus is excellent in performance; however, it is expensive due to the use of the cable and of the non-contact relay. The cable is made by enclosing an ordinary electric wire with a steel sheath to provide two functions: transmission of signal and strength against forces exerted thereon. Production of such a cable is expensive. The use of the transmitter and the receiver and related circuits costs a lot of money, too.

Therefore, the present invention is intended to alleviate or even obviate the drawbacks encountered in prior art.

SUMMARY OF INVENTION

It is the primary objective of the present invention to provide a water-monitoring apparatus capable of automatically tracing water level.

It is another objective of the present invention to provide a water-monitoring apparatus including a sensor, a buoy for carrying the sensor, a tension cable for tying the buoy to a position by the water and a signal wire for connecting the sensor with a monitor device wherein the tension cable and the signal wire are both free of tangle.

According to an aspect of the present invention, a water-monitoring apparatus includes a frame installed in a proper position by water. A reel is mounted on the frame. A constant force device is used to exert a constant force on the reel. A tension cable including a lower end and an upper end is wound on the reel. A buoy is connected with the tension cable. A detecting device is used for detecting at least one water quality parameter. The detecting device is carried by means of the buoy. The detecting device is connected with a monitor device through a signal wire. The signal wire includes a helical section extending around a lower section of the tension cable. The helical section enables the signal wire to automatically adjust a distance between its two ends according to the position of the buoy.

BRIEF DESCRIPTION OF DRAWINGS

The present invention will be described through illustration of some preferred embodiments with reference to the attached drawings wherein.

DETAILED DESCRIPTION OF EMBODIMENTS

First Embodiment

Figure 1:
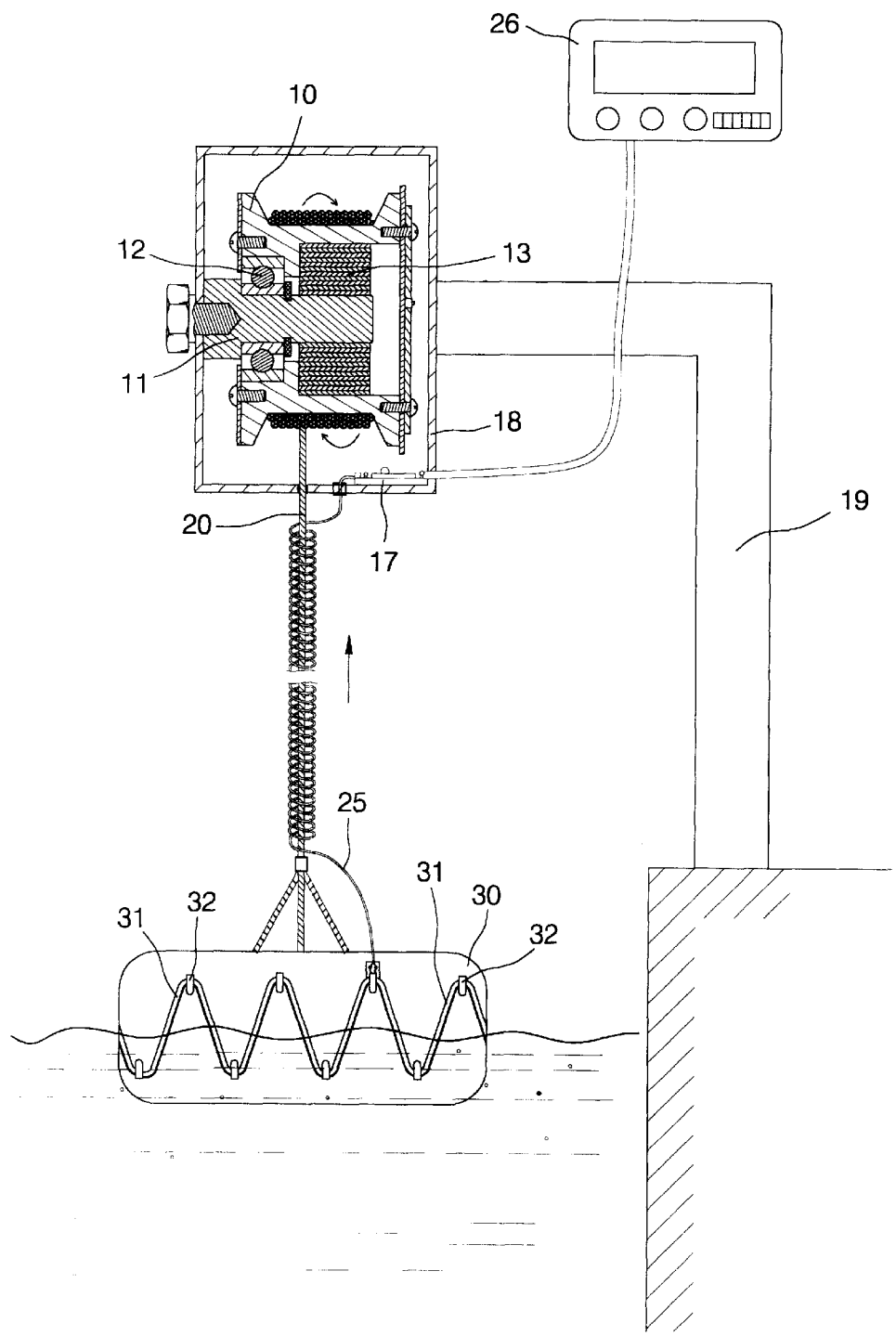
FIG. 1 is a partly cross-sectional elevation of a water-monitoring apparatus according to a first embodiment of the present invention, showing a buoy in a first position.

FIG. 1 shows a water-monitoring apparatus according to an embodiment of the present invention. The water-monitoring apparatus is installed in an appropriate position by the water.

The water-monitoring apparatus includes a box 18 for supporting a number of components thereof (to be described). A frame 19 includes a first end secured to the bank and a second end extending to a position above the water surface. The box 18 is attached to the second end of the frame 19.

A shaft 11 is mounted on a wall of the box 18. A reel 10 is mounted on a middle section of the shaft 11 by means of a bearing 12 so that the reel 10 is allowed to rotate with respect to the shaft 11. The reel 10 includes a cylindrical body and two flanges each formed at an end of the cylindrical body.

A coil spring 13 is connected between the shaft 11 and the reel 10. The coil spring 13 includes a first end connected with a second end of the shaft 11 and a second end connected with the reel 10. The coil spring 13 is selected so that when deformed within an appropriate range it provides a substantially constant force to the reel 10.

A tension cable 20 is wound on the reel 10. The tension cable 20 includes an upper end and a lower end. The upper end of the tension cable 20 is secured to the reel 10. A buoy 30 is connected with the tension cable 20. A number of hooks 32 are provided on a periphery of the buoy 30. A hydrocarbon sensor 31 is in the form of a cable hooked on the hooks 32. Thus, the hydrocarbon sensor 31 is secured to buoy 30 and arranged in a wave-like shape. In this embodiment, the hydrocarbon sensor 31 is AMC-5016 (1932TC) made by Armstrong Monitoring Corporation. The wave-shaped arrangement and characteristics of the hydrocarbon sensor 31 are not described in detail for not being the spirit of the present invention.

A signal wire 25 is connected with the hydrocarbon sensor 31 at an end and is connected with a circuit board 17 at a second end. The circuit board 17 is in turn connected with a monitor device 26. The signal wire 25 includes a helical section winding around a lower section of the tension cable 20.

In use, the buoy 30 is deployed on the water surface so that the hydrocarbon sensor 31 can contact a layer of hydrocarbon, if any, on the water surface. The buoy 30 floats on the water surface. While floating, the buoy 30 is subject to the gravity, a floating force exerted by the water and a tensile force exerted by the tension cable 20. There is a balance between these forces.

The tensile force exerted by the tension cable 20 results from the torque exerted on the reel 10 by the coil spring 13. As mentioned, when deformed within a range, the coil spring 13 exerts a substantially constant force on the reel 10.

Thus, when the length of the tension cable 20 extending from the reel 10 changes within a range, the tension cable 20 exerts a substantially constant tensile force on the buoy 30.

Figure 2:
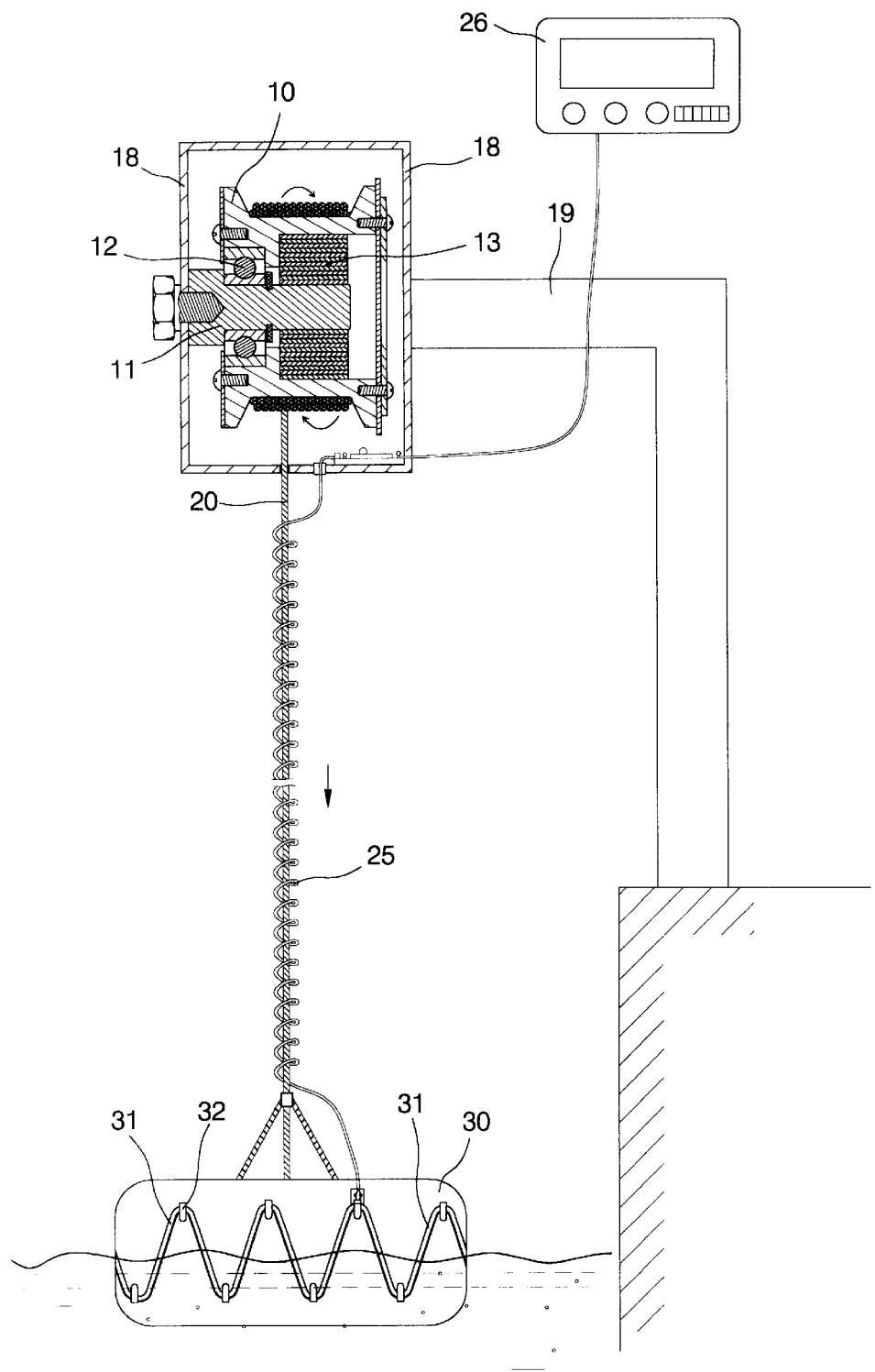
FIG. 2 is an elevation similar to FIG. 1, but showing the buoy in a second position.

When the water level changes from a position shown in FIG. 1 to a position shown in FIG. 2 or vice versa, the length of the tension cable 20 extending from the reel 10 is accordingly adjusted while the tension cable 20 exerts a substantially constant tensile force on the buoy 30. Since the tensile force and the gravity exerted on the buoy 30 remain the same, the floating exerted on the buoy 30 remains the same in order to maintain the balance of forces. In other words, a substantially constant volume of the buoy 30 is immerged in the water. Accordingly, the hydrocarbon sensor 31 is always in contact with the water.

Advantages

A level-tracing water-monitoring apparatus of the present invention provides advantages. Firstly, the tension cable 20 and the signal wire 25 are both free of tangle. The tension cable 20 is free of tangle due to the coil spring 13 connected between the reel 10 and shaft 11. The signal wire 25 is free of tangle due to the helical section automatically adjusting a distance between its two ends according to the motion of the buoy 30. Secondly, the total cost is low. A tension cable is used to take tensile forces and a signal wire used to transmit signals and they are separate and the total cost of separate tension cable and signal wire is lower than that of an electric wire wrapped with a steel sheath. Furthermore, the sensor 31 is simply and directly connected with the circuit board 17 through a simple and low-cost signal wire without the use of a complicated and expensive non-contact relay.

Second Embodiment

Figure 3:
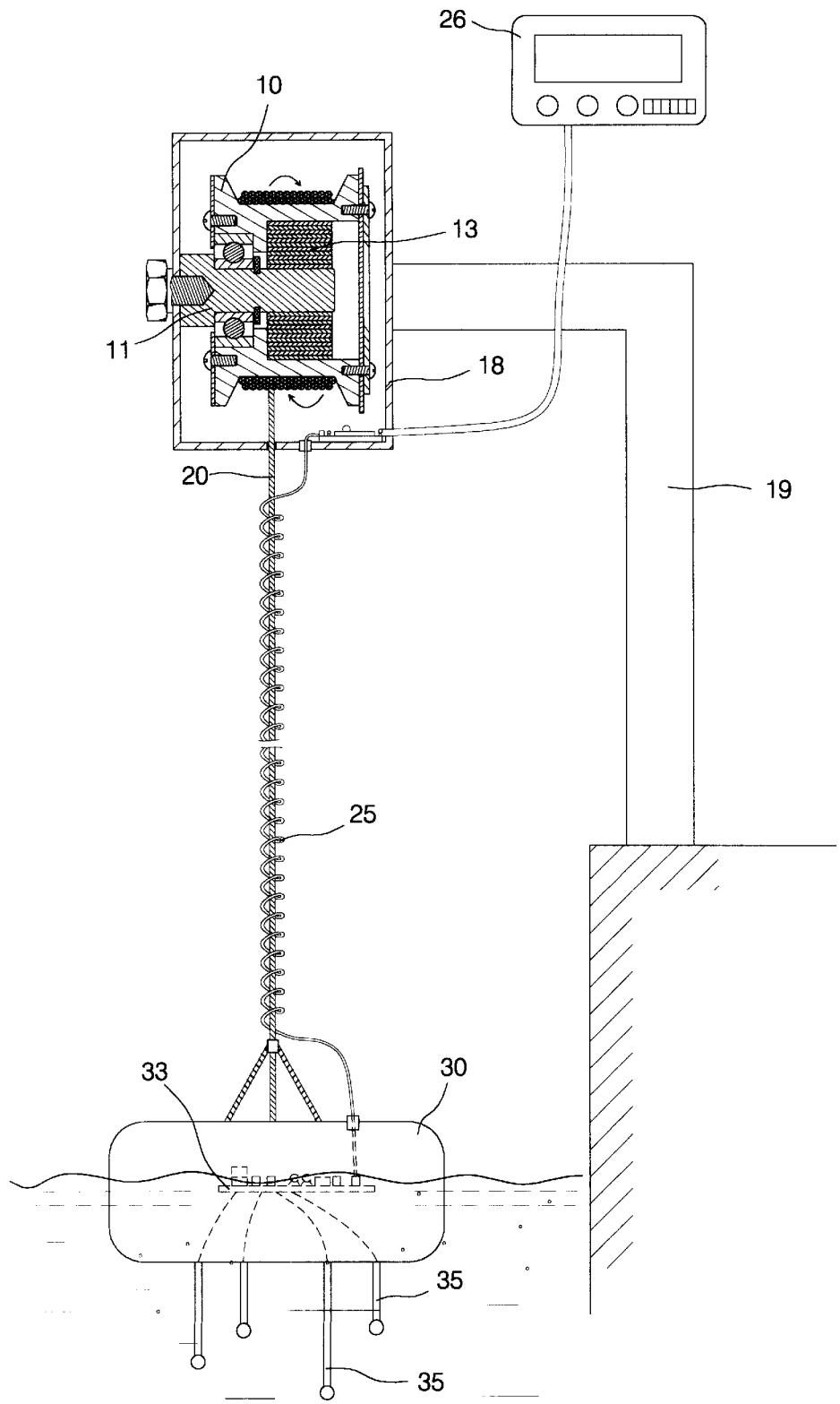
FIG. 3 is a partly cross-sectional elevation of a water-monitoring apparatus according to a second embodiment of this invention.

FIG. 3 shows a water-monitoring apparatus according to a second embodiment of the present invention. The hydrocarbon sensor 31 of the first embodiment is replaced with a number of sensors 35 in the second embodiment. Each sensor 35 is used to produce a signal representative of an environmental parameter and, more particularly, a water quality parameter such as pH, temperature, oxygen content, conductivity, chlorine content, turbidity, heavy metal content, etc. The signal wire 25 is electrically connected through the circuit board 33 with the sensors 35. The circuit board 33 may be designed to periodically acquire the primary signals from the sensors 35, e.g., once every minute, and to stay in a power-saving mode for the rest of every minute.

Third Embodiment

Figure 4:
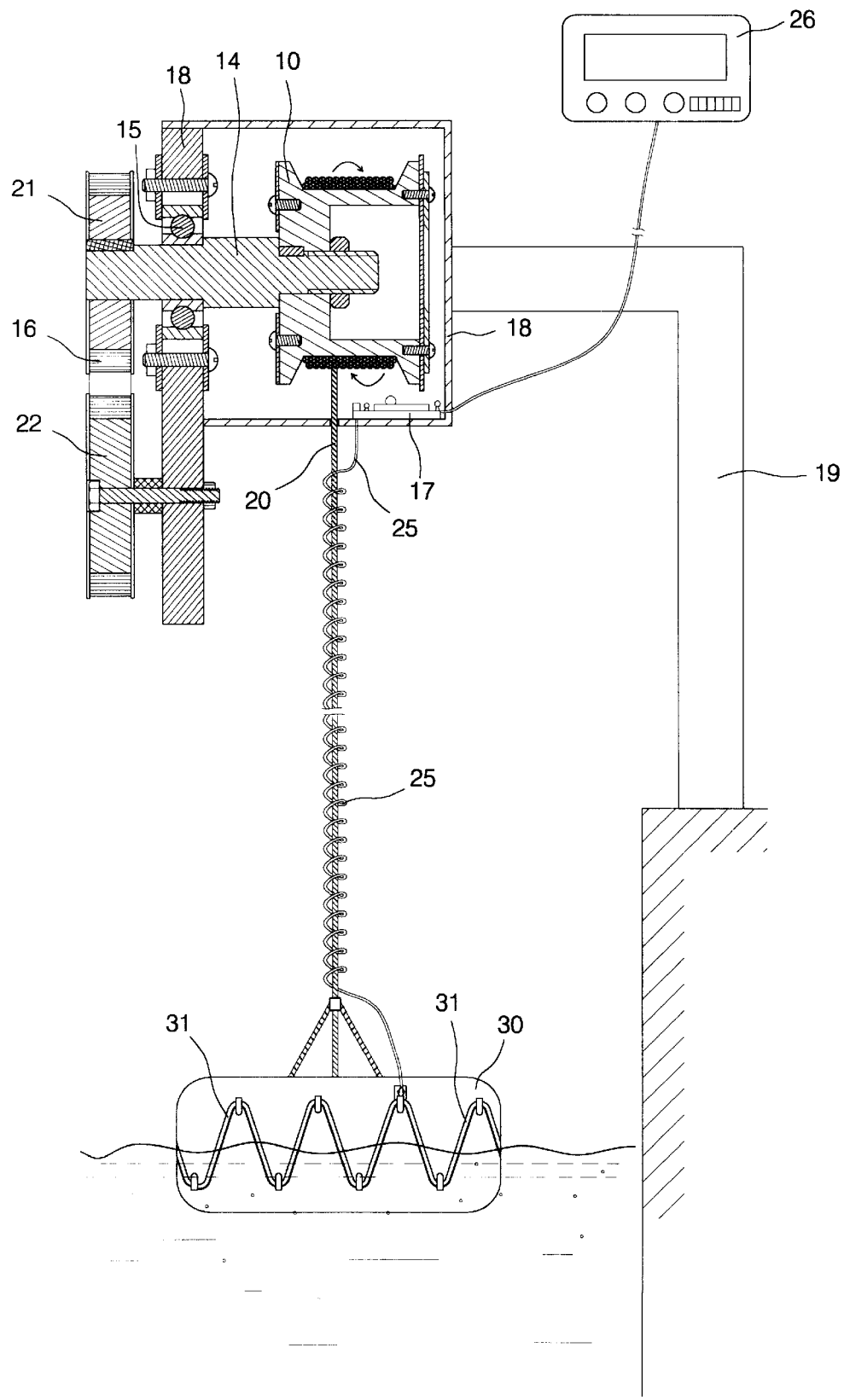
FIG. 4 is a partly cross-sectional elevation of a water-monitoring apparatus according to a third embodiment of this invention.

FIG. 4 shows a third embodiment of the present invention. The coil spring 13 of the first and second embodiments is replaced with a constant force motor spring 16 because the latter provides a force varying within a smaller range. An axle 14 is mounted on a wall of the box 18 by means of a bearing 15. A first drum 21 is secured to the axle 14. A second drum 22 is mounted on the wall of the box 18 in a rotational manner. The constant force motor spring 16 includes a first section connected with and wound on the first drum 21 and a second section connected with and wound on the second drum 22. The axle 14 is connected with the reel 10 so that they are allowed to rotate together. Thus, the constant force motor spring 16 exerts a constant force on the reel 10 through the axle 14.

Fourth Embodiment

Figure 5:
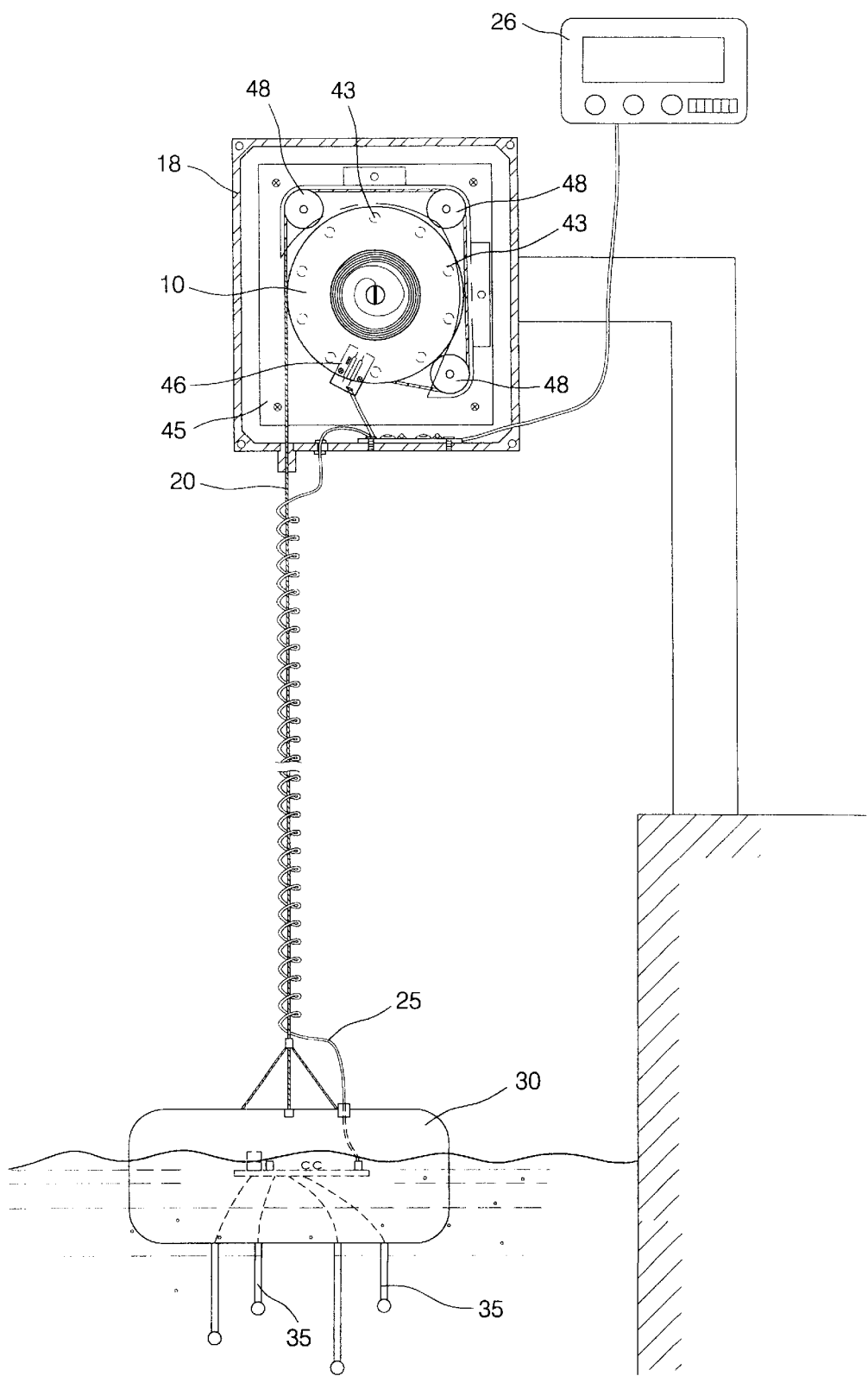
FIG. 5 is a partly cross-sectional elevation of a water-monitoring apparatus according to a fourth embodiment of this invention.

FIG. 5 shows a water-monitoring apparatus according to a fourth embodiment of the present invention including a level-determining device. The level-determining device includes a number of magnets 43 mounted on one of the flanges of the reel 10. A magnetic detector 46 is attached to a plate 45 installed in the box 18. When the buoy 30 moves together with the water surface, the reel 10 rotates and the magnets 43 move. Whenever a magnet 43 moves past the magnetic detector 46, the magnetic detector 46 produces a signal indicating its direction. Such signals are sent to the monitor device 26 that determines how much the float 30 changes its position.

A number of rollers 48 are mounted on the plate 45 for guiding the rollers 48. A device as claimed in U.S. Pat. No. 6,269,547 issued to the present applicant is used to wind the tension cable 20 on the reel 10 in good order.

Fifth Embodiment

Figure 6:
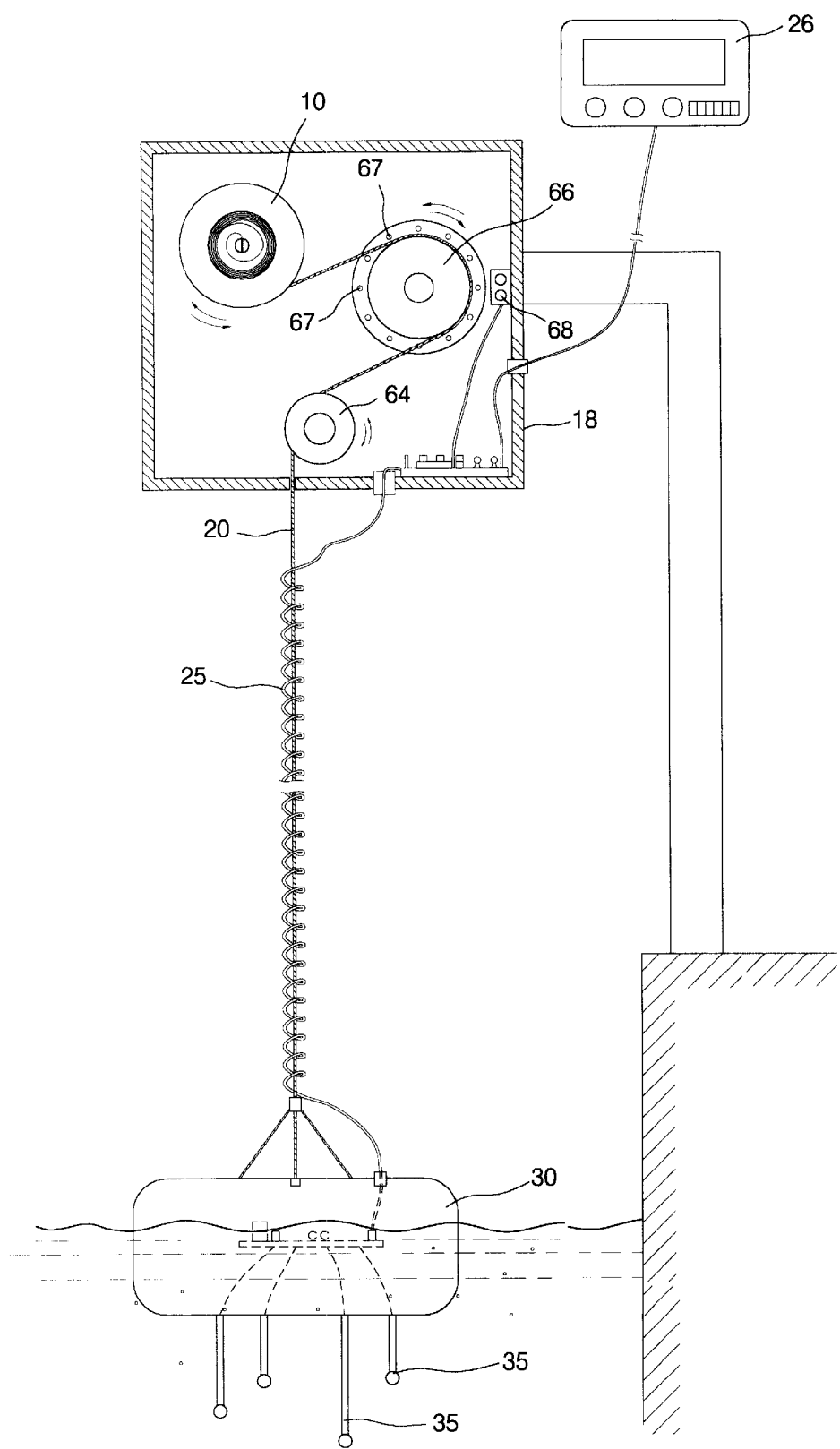
FIG. 6 is a partly cross-sectional elevation of a water-monitoring apparatus according to a fifth embodiment of this invention.

FIG. 6 shows a water-monitoring apparatus according to a fifth embodiment of the present invention with another level-determining device. A section of the tension cable 20 is wound on a pulley 66 mounted on the box 18. Thus, the tension cable 20 rotates the pulley 66 as the buoy 30 rises or falls together with the water surface. A number of magnets 67 are evenly arranged near or on the periphery of the pulley 66. A magnetic detector 68 is located in the box 18 for detecting every magnet 67 passing by. Whenever a magnet 67 moves past the magnetic detector 68, the magnetic detector 68 produces a signal indicating its direction. Such signals are sent to the monitor device 26 that determines how much the float 30 changes its position.

The tension cable 20 is further wound on a pulley 64 mounted on the wall of the box 18, thus changing the direction of the tension cable 20 and increasing the length of the tension cable 20 wound on the pulley 66 to prevent the tension cable 20 from sliding on the pulley 64.

The present invention has been described in relation to some embodiments. It is obvious that modifications and variations can be derived from the above-described embodiments by those skilled in the art. The embodiments are described with reference to the drawings for illustrative purposes only and are not intended to limit the scope of the present invention that can only be limited by the attached claims.

What is claimed is:

1. A water-monitoring apparatus comprising:
   a frame (19) being installed near water;
   a reel (10) being mounted on the frame (19);
   a tension cable (20) being wound on the reel (10) and including a lower end and an upper end;
   a buoy (30) being connected with the tension cable (20);
   a control device being connected with the reel (10) wherein when the water level changes, the control device rotates the reel (10) so as to adjust a length of the tension cable (20) extending from the reel (10) for allowing the buoy (30) to just float on the water surface;
   a detecting device being carried via the buoy (30) for detecting at least one environmental characteristic and for producing at least one signal representative of the at least one environmental characteristic;
   a signal wire (25) being electrically connected with the detecting device and including a helical section for automatically adjusting a distance between its two ends according to the position of the buoy (30), the helical section of the signal wire (25) being wound around a lower section of the tension cable (20); and
   a monitor device (26) being electrically connected with the signal wire.

2. The water-monitoring apparatus as set forth in claim 1 wherein the control device is a constant force device for exerting a constant force on the reel (10).

3. The water-monitoring apparatus as set forth in claim 2 wherein the constant force device is a coil spring (13) including a first end attached to the frame (19) and a second end attached to the reel (10).

4. The water-monitoring apparatus as set forth in claim 2 comprising a shaft (11) mounted on the frame (19), the reel (10) being mounted on the shaft (11).

5. The water-monitoring apparatus as set forth in claim 4 wherein the constant force device is a coil spring (13) including a first end attached to the shaft (11) and a second end attached to the reel (10).

6. The water-monitoring apparatus as set forth in claim 2 comprising a shaft (14) mounted on the frame (19) in a rotational manner, the reel (10) being mounted on the shaft (14).

7. The apparatus as set forth in claim 6 wherein the constant force device is a constant force motor spring.

8. The water-monitoring apparatus of claim 7 wherein the constant force motor spring comprises:
   a first drum (21) being secured to the shaft (14);
   a second drum (22) being rotationally mounted on the frame (19); and
   a spring (16) wound on the first drum (21) and the second drum (22).

9. The water-monitoring apparatus as set forth in claim 1 wherein the detecting device includes a sensing cable (31) mounted on the buoy (30), thus forming a plurality of sensing sections for detecting a layer of hydrocarbon on water.

10. The water-monitoring apparatus of claim 9 wherein the sensing cable (30) is formed of conductive polymer including a first resistance in the air or water and a second resistance larger than the first resistance when contacting hydrocarbon.

11. The water-monitoring apparatus of claim 1, further comprising a plurality of hooks (32) mounted on a periphery of the buoy (30) for engagement with various portions of the sensing cable (31), thus forming the sensing cable (31).

12. The water-monitoring apparatus as set forth in claim 1 wherein the detecting device includes at least one sensor (35) for producing at least one primary signal representative of a water quality parameter.

13. The water-monitoring apparatus as set forth in claim 12 wherein the detecting device includes a sensor control board (33) for converting the primary signal to an electric signal.

14. The water-monitoring apparatus as set forth in claim 13 wherein the sensor control board (33) periodically acquires signals from the sensors and is kept in a power-saving mode for the rest of the time.

15. The water-monitoring apparatus as set forth in claim 13 wherein the sensor control board (33) is received in the buoy (30).

16. The water-monitoring apparatus as set forth in claim 1 comprising a level-determining device for determining the water level.

17. The water-monitoring apparatus as set forth in claim 16 wherein the level-determining device includes:
   a number of magnets (43) evenly mounted on a flange of the reel (10), wherein when the water level changes the buoy (30) moves, thus causing the reel (10) and therefore the magnets (43) to rotate in a direction; and
   a magnetic detector (46) located in the box (18) for detecting each magnet (43) passing by, wherein the magnetic detector (46) determines how much the water level rises or falls by detecting how many magnets (43) pass by and in what direction.

18. The water-monitoring apparatus as set forth in claim 16 wherein the level-determining device includes:
   a pulley (66) mounted on the wall of the box (18), a length of the tension cable (20) being wound on the pulley (66) so that the tension cable (20) rotates the pulley (66) as the buoy (30) rises or falls;
   a number of magnets (67) evenly arranged near or on the periphery of the pulley (66), wherein when the water level changes, the buoy (30) moves, thus causing the pulley (66) and therefore the magnets (67) to rotate in a direction; and
   a magnetic detector (68) received in the box (18) for detecting each magnet (67) passing by, wherein the magnetic detector (68) determines how much the water level rises or falls by detecting how many magnets (67) pass by and in what direction.

19. The water-monitoring apparatus as set forth in claim 18 wherein the level-determining device includes a second pulley (64) mounted on the frame (19) so that the tension cable (20) can be wound on the pulley (64).

* * * * *